United States Patent
Owman

(10) Patent No.: US 6,489,442 B1
(45) Date of Patent: Dec. 3, 2002

(54) HEPTAHELIX RECEPTOR AND ITS USE

(75) Inventor: Christer Owman, Lund (SE)

(73) Assignee: Owman Invest, Ltd., Lund (SE)

( * ) Notice: Subject to any disclaimer, the term of this patent is extended or adjusted under 35 U.S.C. 154(b) by 0 days.

(21) Appl. No.: 09/170,068

(22) Filed: Oct. 13, 1998

Related U.S. Application Data

(60) Provisional application No. 60/063,494, filed on Oct. 22, 1997.

(51) Int. Cl.$^7$ .......................... C07K 1/00; C07K 14/00; C07K 17/00; C07K 16/00; G01N 33/574

(52) U.S. Cl. ...................... 530/350; 530/402; 435/7.2; 435/7.23

(58) Field of Search .............................. 530/402, 300, 530/350; 435/7.2, 7.23

(56) References Cited

U.S. PATENT DOCUMENTS 5,350,836 A * 9/1994 Kopchick et al.
5,882,925 A * 3/1999 Falb

OTHER PUBLICATIONS

Harrison JK, Barber CM, Lynch KR. cDNA cloning of a G–protein–coupled receptor expressed in rat spinal cord and brain relateted to chemokine receptors. Neurosci Lett. Mar. 14, 1994;169(1–2)85–89.*
Vukicevic et al. PNAS USA 93:9021–9026, 1996.*
Massague J. Cell 49:437–8, 1987.*
Pilbeam et al. Bone 14:717–720, 1993.*
Skolnick et al. Trends in Biotech. 18:34–39, 2000.*
Bork P. Genome Research 10:398–400, 2000.*
Doerks et al. Trends in Genetics 14:248–250, 1998.*
Smith et al. Nature Biotechnology 15:1222–1223, 1997.*
Brenner SE. Trends in Genetics 15:132–133, 1999.*
Bork et al. Trends in Genetics 12:425–427, 1996.*
Akbar, G.K.M., et al., "Molecular Cloning of a Novel P2 Purinoceptor from Human Erythroleukemia Cells", J. Biol. Chem., 271:18363–18367 (1996).
Herold, C.L., et al., "Lack of Nucleotide–Promoted Second Messenger Signaling Responses in 1321N1 Cells Expressing the Proposed P2Y Receptor, p2y7", Biochem. and Biophys. Res. Comm., 235:717–721 (1997).
Methner, A., et al., "A Novel G Protein–Coupled Receptor with homology to Neuropeptide and Chemoattractant Receptors Expressed During Bone Development", Biochem. and Biophys. Res. Comm., 233:336–342 (1997).
Metters, K.M., "Leukotriene receptors", J. Lipid Mediators Cell Signaling, 12:413–427 (1995).
Owman, C., et al., "Cloning of cDNA Encoding a Putative Chemoattractant Receptor", Genomics, 37:187–194 (1996).
Owman, C., et al., "Leukotriene $R_4$ is the Functional Ligand Binding to and Activating the Cloned Chemoattractant Receptor, CMKRL1", Biochem. and Biophys. Res. Comm., 240:162–166 (1997).
Owman, C., et al., "Molecular Cloning and Tissue Distribution of cDNA Encoding a Novel Chemoattractant–like Receptor", Biochem. and Biophys. Res. Comm., 241:390–394 (1997).
Raport, C.J., et al., "New members of the chemokine receptor gene family", J. of Leukocyte Biol., 59:18–23 (1996).
Yokomizo, T., et al., "A G–protein–coupled receptor for leukotriene $B_4$ that mediates chemotaxis", Nature, 387:620–624 (1997).
Owman C, et al. Cloning of human cDNA encoding a novel heptahelix receptor expressed in Burkitt's lymphoma and widely distributed in brain and peripheral tissues. Biochem. Biophys. Res. Comm. vol. 228, pp. 285–292, 1996.*
Feng Y and Gregor P. Cloning of a novel member of the G–protein–coupled receptor family related to peptide receptors. Biochem. Biophys. Res. Comm. vol. 231, pp. 651–654, 1997.*

* cited by examiner

*Primary Examiner*—Lorraine Spector
*Assistant Examiner*—Robert S. Landsman
(74) *Attorney, Agent, or Firm*—Finnegan, Henderson, Farabow, Garrett & Dunner, LLP

(57) ABSTRACT

A full-length cDNA encoding a 375-amino-acid protein contains seven regions of hydrophobic amino acids representing membrane-spanning domains of a heptahelix receptor, tentatively named CMKRL2. It shows nearly 30% overall identity with the high-affinity IL8 receptor and similar degree of homology with other chemoattractant receptors, including the coreceptors for HIV-1. Receptor expression was ubiquitous in brain and in peripheral tissue as well as in Burkitt's lymphoma (irrespective of EBV status). The receptor and the gene encoding the receptor are useful for detecting Burkitt's lymphoma.

10 Claims, 6 Drawing Sheets

```
  1    M  D  V  T  S  Q  A  R  G  V  G  L  E  M  Y  P  G  T  A  Q  P  A  A  P  N  T  T  S  P  E  L  N  L  S  H  P  L  L  G  T
  1   Atggatgtgacttcccaagcccggggcggtgggcctggagatgtaccaggcaccgcgccagcctgccgcccccaacaccacctcccccgagctcaacctgtcccaccccgctcctgggcacc  120
                                                                                          I
 41    A  L  A  N  G  T  G  E  L  S  E  H  Q  Q  Y  V  I  G  L  F  L  S  C  L  Y  T  I  F  L  F  P  I  G  F  V  G  N  I  L  I
121   gccctggccaatggcacaggcgagctctcggagcaccagcagtacgtgatcggcctgttcctctgcctgtacaccatcttcctcttcccatccccatcggcttcgtgggcaacatcctgatc  240
                                                                       II
 81    L  V  V  N  I  S  F  R  E  K  M  T  I  P  D  L  Y  F  I  N  L  A  V  A  D  L  I  L  V  A  D  S  L  I  E  V  F  N  L  H
241   ctggtggtgaacatcagctccgcgagaaagatgaccatccccgacctgtacttcatcaacctggcggtggccgacctcatcctggtggccgactccctcatcgaggtgttcaacctgcac  360
                                              III
121    E  R  Y  Y  D  I  A  V  L  C  T  F  M  S  L  F  L  Q  V  N  M  Y  S  S  V  F  F  L  T  W  M  S  F  D  R  Y  I  A  L  A
361   gagcggtactacgacatcgcagtgctgtgcaccttcatgagcctgttcctgcaggtcaacatgtacagcagcgtcttcttcctcacctggatgagcttcgaccgctacatcgccctggcc  480
                                                                                       IV
161    R  A  M  R  C  S  L  F  R  T  K  H  H  A  R  L  S  C  G  L  I  W  M  A  S  V  S  A  T  L  V  P  F  T  A  V  H  L  Q  H
481   agggccatgcgctgcagcctgttccgcaccaagcaccacgcccggctgagctgtgccctcatctggatggccagcgtgtccgccacgctggtgcccttcacggccgtgcacctgcagcac  600
                                                                 V
201    T  D  E  A  C  F  C  F  A  D  V  R  E  V  Q  W  L  E  V  T  L  G  F  I  V  P  F  A  I  I  G  L  C  Y  S  L  I  V  R  V
601   accgacgaggcctgcttctgtttcgccgatgtccgggaggtgcagtggctcgaggtcacgctggcttcatcgtcccttcgccatcatcggcctgtgctactccctcattgtccgggtg  720
                                                                                        VI
241    L  V  R  A  H  R  H  R  G  L  R  P  R  R  Q  K  A  L  R  M  I  L  A  V  V  L  V  F  F  V  C  W  L  P  E  N  V  F  I  S
721   ctggtcagggcgcaccggcaccggggctgcgcccccgccggcagaaggcgctccgcatgatcctcgcggtggtgctggtcttcttcgtctgctggctgcccgagaacgtcttcatcagc  840
                                                VII
281    V  H  L  L  Q  R  T  Q  P  G  A  A  P  C  K  Q  S  F  R  H  A  H  P  L  T  G  H  I  V  N  L  A  A  F  S  N  S  C  L  N
841   gtgcacctcctgcagcggacccagccaggcgcagccccctgcaagcagtcttttccgccatgcccaccccctacgggccacattgtcaacctgcccttctccaacagctgcctaaac  960
321    P  L  I  Y  S  F  L  G  E  T  F  R  D  K  L  R  L  Y  I  E  Q  K  T  N  L  P  A  L  N  R  F  C  H  A  A  L  K  A  V  I
961   cccctcatctacagctttctcggggagaccttcagggacaagctgaggctgtacattgagcagaaaacaaattgccggccctgaaccgcttctgtcacgctgccctgaaggccgtcatt  1080
361    P  D  S  T  E  Q  S  D  V  R  F  S  S  A  V  *      375   (SEQ ID NO:2)
1081  ccagacagcaccgagcagtcggatgtgaggttcagcagtgccgtgtag        1128  (SEQ ID NO:1)

FIG. 1
```

HEPTAHELIX RECEPTOR AND ITS USE

CROSS-REFERENCE TO RELATED APPLICATION

This regular U.S. patent application claims the benefit of U.S. provisional patent application No. 60/063,494, filed Oct. 22, 1997, the entire disclosure of which is relied upon and incorporated herein by reference.

BACKGROUND OF THE INVENTION

This invention relates to a new chemoattractant receptor and its use. More particularly, this invention relates to cDNA encoding a novel heptahelix receptor widely distributed in brain and peripheral tissues. This invention also relates to the use of the receptor for detecting Burkitt's lymphoma cells.

The G-protein coupled (heptahelix) membrane receptors (1) receive chemical signals in cell communication both in CNS and in the peripheral tissues. Interest has recently focused also on the immune system because this receptor type is recognized by many chemoattractant peptides, the model substances being IL8 (2,3), and heptahelix receptors are now recognized also among cluster determinant antigens in immune cells, i.e., CDw78 (4) and CD97 (5).

In addition, the G-protein coupled receptors may be involved in other functional mechanisms, such as viral pathogenesis. Thus, the human cytomegalovirus shows structural homology with heptahelix receptors (6) and encodes a functional chemokine receptor (7), and *Herpesvirus saimiri* exerts "molecular piracy" entry of HIV-1 into CD4-positive cells is mediated by two distinct chemoattractant receptors (9–10). *Herpesvirus saimiri* is closely related to the B lymphotropic Epstein-Barr virus (EBV). This is implicated in several human malignancies, such as Burkitt's lymphoma, which expresses BLR1, the first example of a heptahelix (chemokine-like) receptor identified specifically in the lymphocyte lineage of the hematopoietic system (11).

Because of the continuing interest in chemoattractant receptors, there exists a need in the art for the identification of new receptors and the elucidation of their structure so that the function of these receptors in humans can be determined.

In particular, there exists a need in the art for sequence information on such receptors, including DNA and amino acid sequences, to enable the isolation and characterization of particular receptors as well as structurally related receptors. The identification of receptors associated with pathogenic conditions would be particularly advantageous in assays for the identification of these conditions in susceptible individuals.

SUMMARY OF THE INVENTION

Accordingly, this invention aids in fulfilling these needs in the art. More particularly, this invention provides a B-cell derived heptahelix receptor that is strongly expressed in brain and peripheral tissues. The receptor can be detected in Burkitt's lymphoma cells. A receptor of human origin shows structural identity with both the IL8 receptors and with the co-receptors for HIV-1.

More particularly, the present invention provides isolated heptahelix receptors and DNA sequences encoding these heptahelix receptors. Such DNA sequences include (a) cDNA clones having a nucleotide sequence derived from the coding region of a native heptahelix receptor gene of the invention; (b) DNA sequences that are capable of hybridization to the cDNA clones of (a) under moderately stringent conditions and which encode biologically active heptahelix receptor molecules; and (c) DNA sequences that are degenerate as a result of the genetic code to the DNA sequences defined in (a) and (b) and which encode biologically active heptahelix receptor molecules.

The present invention also provides recombinant expression vectors comprising the DNA sequences defined above, recombinant heptahelix receptor molecules produced using the recombinant expression vectors, and processes for producing the recombinant heptahelix receptor molecules using the expression vectors.

The present invention further provides isolated or purified protein compositions comprising heptahelix receptor of the invention.

In one embodiment of the invention, a heptahelix receptor of the invention has the following amino acid sequence and corresponding nucleotide sequence:

```
  1   M  D  V  T  S  Q  A  R  G  V  G  L  E  M  Y  P  G  T  A  Q  P  A  A  P  N  T  T  E  P  E  L  M  S  P  L  L  G  T         40
  1  atggatgtgacttcccaagccggggcgtggggctggagatgtaccaggcaccgcagccgcggcccaacaccacccctgagcctcaacctgtccaccaccgtcctggcacc             120

41   A  L  A  N  G  T  G  E  L  S  E  H  Q  Q  Y  V  I  G  L  F  L  S  C  L  Y  T  I  F  L  F  P  I  G  F  V  G  M  I  L  I    80
121  gccctggcaaatggcacaggtgagctctcggagcaccaggagtacgtgggcctgttcctctcctgtctctacacaatcttcctcttcccatcgggcttcgtgggcaacatcctgatc       240
                                                                    I 81   L  V  V  M  I  S  F  R  I  R  M  T  I  P  D  L  Y  Y  I  N  L  A  V  A  D  L  I  L  V  A  D  S  L  I  E  V  F  N  L  N   120
241  ctgtggtgatgatcagcttccgcgagaagatgaccatcccgacctgtactacatcaacctggtggcagatctcatcctggtggccgactccctcattgaggtcttcaacctgaac        360
                                      II 121   E  R  Y  Y  D  I  A  V  L  C  T  F  M  S  L  F  L  Q  V  N  M  Y  S  S  V  F  F  L  T  M  M  S  F  D  R  Y  I  A  L  A   160
361  gagcggtactacgatattgccgtcctgtgcaccttcatgtcgctcttcctgcaggtcaacatgtacagctcagtcttcttcctcaccatggatgagcttcgaccgctacatcgccctggcc  480
                               III 161   R  A  M  R  C  S  L  F  R  T  K  N  M  A  R  L  S  C  G  L  I  W  M  A  S  V  S  A  T  L  V  P  F  T  A  V  H  L  Q  M   200
481  agggccatgcgctgctcgctgttccgcaccaagaacatggcccggctgagctgtggcctcatctggatggcatccgtgtcagcaacgctggtgccctccacgctgcaccgtgcaccgcagac   600
                                                        IV 201   T  D  E  A  C  F  C  F  A  D  V  R  E  V  Q  N  L  I  V  T  L  G  F  I  V  P  F  A  I  I  G  L  C  Y  S  L  I  V  R  V   240
601  accgacgaggccgcttctgttcgcggatgtccggagagtgcagtggctcgaggtgcagaacctcatcgtcacgctgggcttcatcgtgcccatcgccatcatcggggtgctactccccatt   720
                                                V 241   L  V  R  A  M  R  N  R  G  L  R  P  R  R  Q  K  A  L  R  M  I  L  A  V  V  L  V  F  F  V  C  W  L  P  A  M  V  F  I  S   280
721  ctgtcaggcgcgcattgcacacggctggacctggggcgcaccggagaaggcgccccgatccttccgctctgtgctcgtgctgcggcctgtctggtgcggagaactgcttcatcagc       840
                                                                                                                 VI 281   V  M  L  Q  R  T  Q  P  G  A  A  P  C  K  Q  S  F  R  M  A  N  P  L  T  G  M  T  V  M  L  A  A  F  S  N  S  C  L  N   320
841  gtcatgcctctgcagcggacccagccgagcagctgccccctgcaagcagtctttccggtatggccaacccctgacggcacattgtaacctcgccgccttccaagcagcctgctaaac         960
                                                VII 321   F  L  I  Y  S  F  L  G  C  T  F  R  D  K  L  R  L  Y  I  K  Q  K  T  N  L  P  A  L  M  R  F  C  H  A  A  L  K  A  V  I   360
961  cccctcatctacagcttcctcggggagtgcacctttcgggacaagctgcgactctacattaagcagaagaccaatttgccggcgctgatgcgcttctgtcatgctgcctgaaggctgtcatt  1080

361   P  D  S  T  E  Q  S  D  V  R  F  S  S  A  V   .  375
1081 ccagacagcaccgagcagagtgatgtcaggttcagcagtgccgtgtag 1128 (SEQ ID NO. 1).
```

The heptahelix receptor compositions of the invention are useful in diagnostic assays for heptahelix receptor, as well as in raising antibodies to heptahelix receptor for use in diagnosis and therapy. In addition, the heptahelix receptor compositions can be used directly in therapy to bind or scavenge chemoattractants, thereby providing a means for regulating the immune activities of chemoattractants. In particular, because the heptahelix receptor of the invention is expressed in Burkitt's lymphoma, the invention is useful for detecting these lymphoma cells, for example, by immunoassay for heptahelix polypeptides of the invention or by detection of all or part of the polynucleotides encoding the receptor of the invention, such as by hybridization assays or amplification reactions.

BRIEF DESCRIPTION OF THE DRAWINGS

This invention will be more fully described with reference to the drawings in which:

FIG. 1 shows the nucleotide sequence of the coding region of Lymc47-2 together with the deduced amino acid sequence of a corresponding heptahelix receptor of the invention, which has been designated CMKRL2. The putative transmembrane segments TMI–TMVII, whose extensions are based on sequence alignments of other heptahelix receptors and include the highly hydrophobic regions illustrated in FIG. 2, are indicated by numbered solid lines. Extracellular domains are the regions before TMI, between TMII and TMIII, between TMIV and TMV, and between TMVI and TMVII.

Corresponding intracellular domains are the regions between TMI and TMII, between TMIII and TMIV, between TMV and TMVI, and the tail following TMVII. Potential glycosylation sites are marked with arrowheads. The sequence data have been deposited with the EMBL/GenBank/DDBJ databases under accession No. Y08162.

Figure 2:
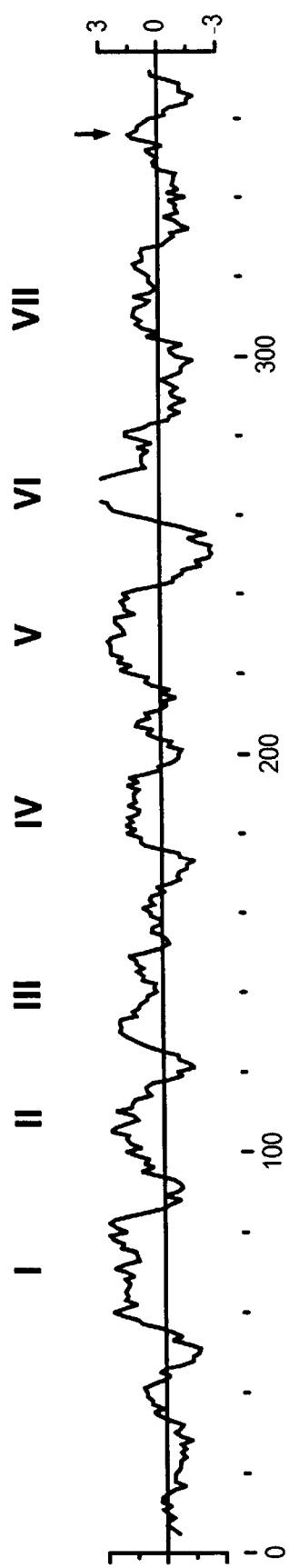

FIG. 2 is the hydropathy pattern of the deduced amino acid sequence of CMKRL2. Positive regions containing maximally hydrophobic amino acids (over a window of 9 in the standard GCG program) are numbered above (I–VII). The arrow points to an anchoring site for the intracellular protein tail. The horizontal scale below shows the amino acid numbers.

Figure 3:
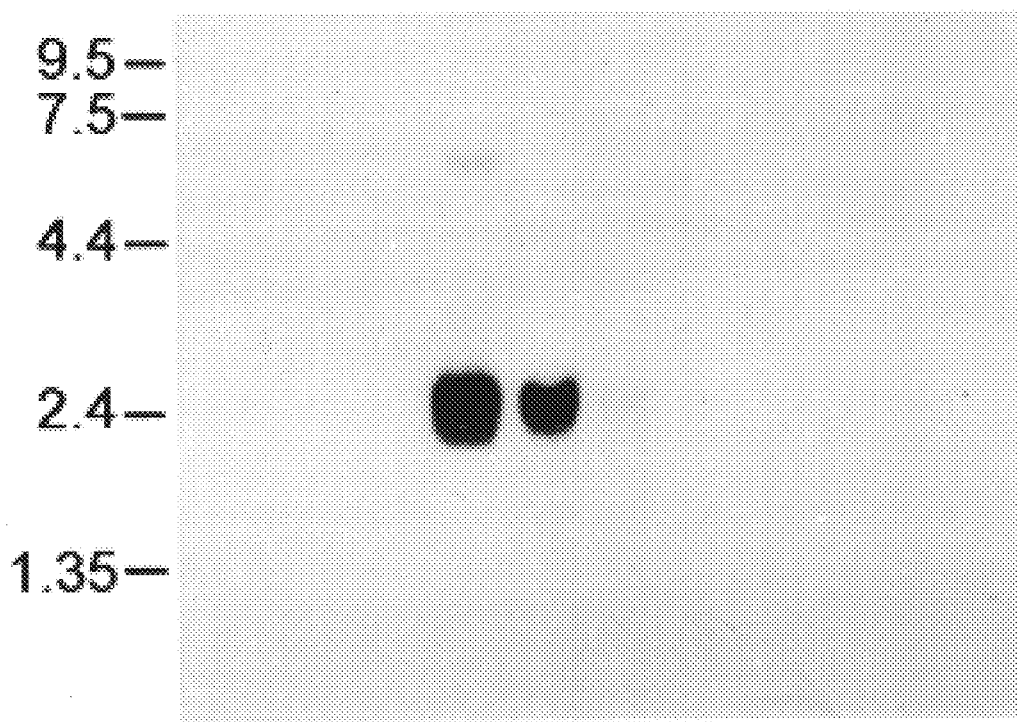

FIG. 3 depicts the results of Northern blot hybridization (2 µg mRNA or 30 µg total RNA per lane) of 11 human tumor cell lines: 1, promyeloic leukemia; 2, HeLa cells; 3, chronic myelogenous leukemia; 4, Burkitt lymphoma Raji; 5, virus-negative lymphoma; 6, Burkitt lymphoma Daudi; 7, B-cell leukemia; 8, lymphoblastic leukemia; 9, colorectal adenocarcinoma; 10, lung carcinoma; and 11, melanoma. Strong hybridization was detected in Raji and also in the virus-negative lymphoma, weak hybridization was detected in Daudi, while other cell lines showed no expression of Lymc47-2, which codes for CMKRL2.

Figure 4:
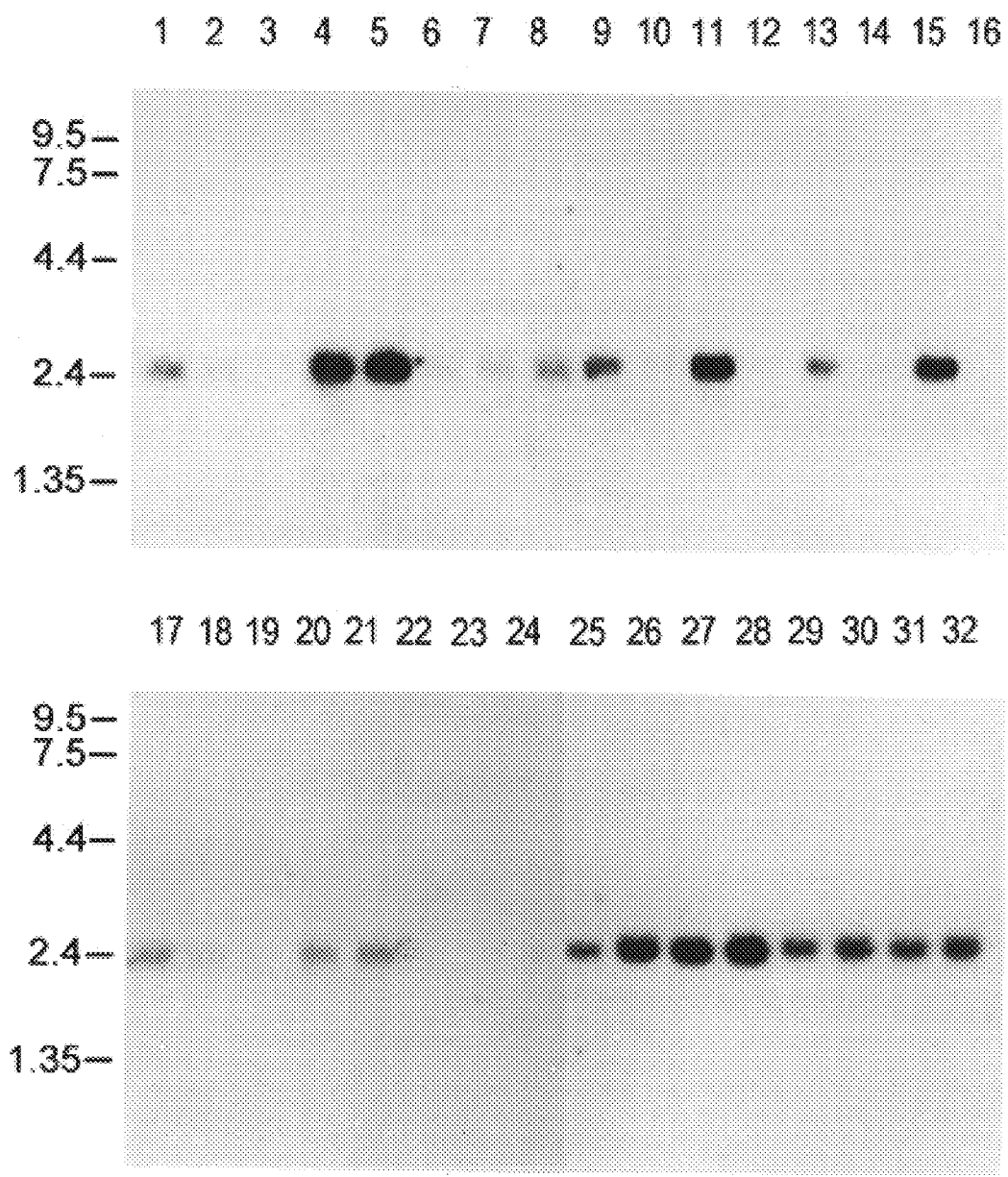

FIG. 4 depicts the results of Northern blot hybridization (2 µg mRNA or 30 µg total RNA per lane) from human tissues following hybridization with Lymc47-2 cDNA probe: 1, heart; 2, brain; 3, placenta; 4, lung; 5, liver; 6, skeletal muscle; 7, kidney; 8, pancreas; 9, spleen; 10, thymus; 11, prostate; 12, testis; 13, ovary; 14, small intestine; 15, colon; 16, peripheral blood leukocytes; 17, lymph node; 18, bone marrow; 19, appendix; 20, fetal liver; 21, peripheral blood mononuclear cells; 22, monocytes; 23, resting B-cells; 24, cerebellum; 25, cerebral cortex; 26, medulla; 27, spinal cord; 28, occipital pole; 29, frontal pole; 30, temporal pole; 31, putamen; and 32, hypothalamus. Signal comparison is discussed hereinafter.

FIGS. 5A and 5B depict the results of chromosome mapping of the receptor of the invention. Fluorescence photomicrographs showing FISH mapping of Lymc47-2, which codes for CMKRL2, are included in the Figure. Panel (A) shows the fluorescent signal in chromosome as indicated by the arrow. Panel (B) shows the same mitotic figure stained with DAPI to identify chromosome 7. Original magnification was ×1300.

Figure 6:
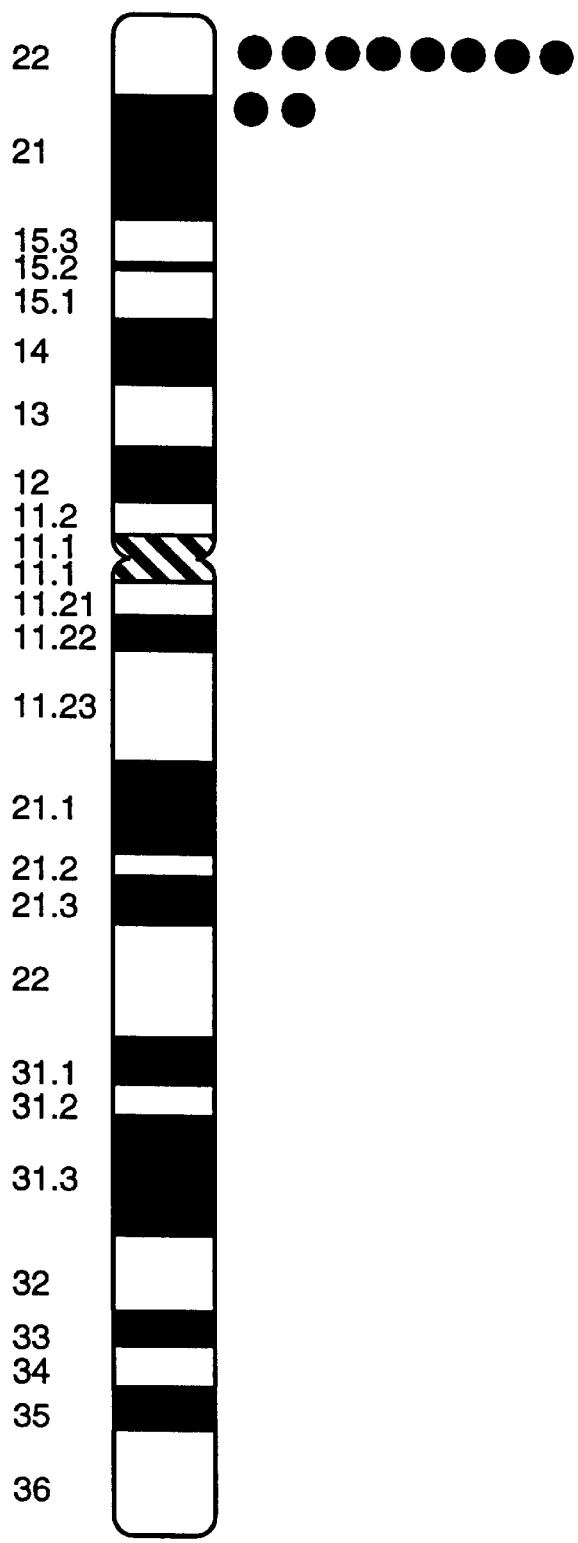

FIG. 6 localizes the position of the gene encoding the receptor of the invention (CMKRL2) to region P22 by of FISH/DAPI mapping. Each dot represents fluorescence signals in duplicate readings on chromosome 7 (diagram composed from 10 photographic images).

DETAILED DESCRIPTION OF THE INVENTION

The native, mature full-length human heptahelix receptor of the invention is a 375 amino acid protein having a molecular weight of about 46 kilodaltons (kDa) as deduced from the number of amino acid residues in the molecule. This heptahelix receptor has been given the designation "CMKRL2". As used herein, the term "heptahelix receptor" refers to proteins and polypeptides having amino acid sequences that are substantially similar to this native, mature, mammalian heptahelix receptor amino acid sequence, and which are biologically active, as defined below, in that they are capable of binding chemoattractant molecules or transducing a biological signal initiated by a chemoattractant or other ligand binding to a cell as CMKRL2 is able to do, or cross-reacting with anti-heptahelix receptor antibodies raised against heptahelix receptor from natural (i.e., nonrecombinant) sources. As used throughout the specification, the term "mature" means a protein expressed in a form lacking a leader sequence as may be present in full-length transcripts of a native gene.

The term "heptahelix receptor" includes, but is not limited to, analogs or subunits of native proteins having seven membrane-spanning or hydrophobic regions and which exhibit at least some biological activity in common with CMKRL2. For example, soluble heptahelix receptor constructs, which possess the seven hydrophobic regions (and are secreted from the cell), and retain the ability to bind chemoattractants are deemed to be heptahelix receptors of the invention.

In the absence of any species designation, heptahelix receptor refers generically to mammalian heptahelix receptor. Similarly, in the absence of any specific designation for deletion mutants, the term heptahelix receptor means all forms of heptahelix receptor, including mutants and analogs that possess heptahelix receptor biological activity.

"Soluble heptahelix receptor" as used in the context of the present invention refers to proteins and polypeptides, or substantially equivalent analogs, having an amino acid sequence corresponding to all or part of the heptahelix receptor, and which are biologically active in that they bind to chemoattractants and other related ligands. Soluble heptahelix receptors include polypeptides that vary from those sequences by one or more substitutions, deletions, or additions, and which retain the ability to bind chemoattractant or inhibit chemoattractant signal transduction activity via cell surface bound heptahelix receptor proteins. Inhibition of chemoattractant signal transduction activity can be determined by transfecting cells with recombinant heptahelix receptor DNAs to obtain recombinant receptor expression. The cells can then be contacted with chemoattractant or other ligand and the resulting metabolic or signal transduction effects examined. If an effect results that is attributable to the action of the chemoattract or other ligand, then the recombinant receptor has signal transduction activity. Procedures for determining whether a polypeptide has signal transduction activity include measurement of adenyl cyclase activity and intracellular calcium measurements.

The group of chemoattractant substances as used in the context of the present invention comprises both the classical chemoattractants and the chemokines. Examples of classical chemoattractants, as one having ordinary skill in the art would appreciate, include but are not limited to LTB4, PAF, fMLP, C3a, and C5a. Furthermore, all subtypes of the chemokines, i.e., alpha, beta, etc., are within the context of the present invention.

The term "isolated" or "purified", as used in the context of this invention to define the purity of heptahelix receptor protein or protein compositions means that the protein or protein composition is separated from its native environment. In one embodiment, the heptahelix receptor can be substantially free of other proteins of natural or endogenous origin. In a preferred embodiment, the receptor can contain less than about 1% by mass of protein contaminants residual of its native environment or production processes. Such compositions, however, can contain other proteins added as stabilizers, excipients, or cotherapeutics.

The term "substantially similar" when used to define either amino acid or nucleic acid sequences means that a particular subject sequence, for example, a mutant sequence, varies from a reference sequence by one or more substitutions, deletions, or additions, the net effect of which is to retain biological activity of the heptahelix receptor as may be determined, for example, in a chemoattractant assay for heptahelix receptor binding. Alternatively, nucleic acid subunits and analogs are "substantially similar" to the specific DNA sequences disclosed herein if: (a) the DNA sequence is derived from the coding region of native, mammalian heptahelix receptor gene of the invention, (b) the DNA sequence is capable of hybridization to DNA sequences of (a) and which encode biologically active heptahelix receptor molecules; or DNA sequences that are degenerate as a result of the genetic code to the DNA sequences defined in (a) or (b) and which encode biologically active heptahelix receptor.

The heptahelix receptor of the invention can be obtained from natural sources or by recombinant techniques using eukaryotic or procaryotic host systems. "Recombinant" as used herein means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system that is essentially free of native endogenous substances. Protein expressed in most bacterial cultures, e.g., E. coli, will be free of glycan. Protein expressed in yeast may have a glycosylation pattern different from that expressed in mammalian cells.

"Biologically active" as used throughout this specification as a characteristic of heptahelix receptors of the invention means that a particular molecule shares sufficient amino acid sequence similarity with embodiments of the present invention to be capable of binding chemoattractant or other ligand, transmitting a stimulus to a cell, for example, as a component of a hybrid receptor construct, or cross-reacting with anti-heptahelix receptor antibodies raised against heptahelix receptor from natural (i.e., nonrecombinant) sources.

"Isolated DNA sequence" refers to a DNA polymer in the form of a separate fragment or as a component of a larger DNA construct, which has been derived from DNA isolated at least once. Preferably, the heptahelix receptor is in substantially pure form, i.e., free of contaminating endogenous materials and in a quantity or concentration enabling identification, manipulation, and recovery of the sequence and its component nucleotide sequences by standard biochemical methods. Such sequences are preferably provided in the form of an open reading frame uninterrupted by internal, nontranslated sequences, or introns, which are typically present in eukaryotic genes. Such a sequence is shown in FIG. 1 for the preferred heptahelix receptor CMKRL2. Genomic DNA containing the relevant sequences can also be used as a source of coding sequences. The genomic location of such DNA is described hereinafter. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the heptahelix receptors of this invention can be assembled from DNA fragments, such as short oligonucleotide linkers, or from a series of oligonucleotides, or by amplification reactions to provide a synthetic gene that is capable of being expressed in a recombinant transcriptional unit. With this background, the characteristics of one embodiment of the invention will now be described in detail.

Using a homology strategy based on conserved regions in previously cloned neurotransmitter receptors for screening of an "unusual" cDNA library from human lymphoblastoid B-cells, a full-length cDNA was obtained that encodes a novel G-protein coupled heptahelix receptor of the invention. It has been named CMKRL2 due to its high degree of identity with chemoattractant receptors and because of the presence of many consensus features shared by other receptors in this subfamily (2).

The heptahelix receptor of the invention has more than 28% homology with CMKRL1, which was recently cloned from the same library (12), but the distribution of the two novel receptors within the immune system is markedly different. CMKRL2, like BLR1 (11), typically shows selective and high expression in Burkitt's lymphoma, irrespective of the EBV status. This indicates that the receptors participate in B-cell functions separate from the viral pathogenetic mechanism (22).

It is notable that the receptor gene for the prominent B-cell differentiation factor IL6, which is a growth factor for myelomas, B-cell hybridomas, as well as activated and EBV-transformed B-cells, is localized near that of the CMKRL2 gene on chromosome 7p21 (23). The B-cells that constitute the source for the presently used cDNA library were immortalized for long-term growth by EBV infection in vitro (24). It is well-known that this transformation leads to recapitulation of features of antigen stimulation and activation of the mature B-cells. This agrees with, on the one hand, the expression of CMKRL2 in spleen and lymph nodes and, on the other, the absence of expression in bone marrow and peripheral blood lymphocytes, as well as in the thymus and T-cell derived tumor cell lines. It may be noted that also another chemoattractant-like Burkitt lymphoma receptor, EBI1/BLR2, is expressed in EBV-transformed B-lymphoblasts (25) and becomes markedly upregulated upon activation of blood lymphocytes with TPA (19).

CMKRL2 is the first, human, chemoattractant-like receptor that is ubiquitously expressed in CNS. The mouse homolog of the BLR1 receptor (11) shows a restricted expression in the granule and Pukinje cell layer of the cerebellum (26). The expression pattern of CMKRL2 would suggest that this receptor is localized in a more universal cell population, such as glial cells. With corresponding reasoning, it is possible that CMKRL2 in peripheral (non-lymphatic) tissues also resides in a general cell compartment, e.g., macrophages. In view of this, the receptor expression seen in fetal liver (but not in adult bone marrow) is probably not associated with hematopoietic mechanisms, but rather reflects hepatic expression in its own right, which would agree with the expression found also in adult liver.

More particularly, using PCR with degenerate primers and screening of a human B-cell lymphoblast cDNA library, a full-length cDNA encoding a 375 amino acid protein was isolated. It contains seven regions of hydrophobic amino acids probably representing membrane-spanning domains of a novel heptahelix receptor, named CMKRL2. It shows nearly 30% overall identity with the high-affinity IL8 receptor and similar degree of homology with other chemoattractant receptors, including the coreceptors for HIV-1, which is contemplated for purposes of this invention to be a ligand for the heptahelix receptor. Measurements of various transduction pathways following application of a panel of known chemoattractants to transfected cells failed to evoke any reproducible response. Receptor expression in spleen and lymph nodes as well as in Burkitt's lymphoma (irrespective of EBV status) supports a functional role in activated B-cells. Receptor message was ubiquitously distributed in normal peripheral tissues and CNS, suggesting that CMKRL2 is expressed in widespread cell populations, such as macrophages and neuroglia.

FIG. 1 shows the coding region of the nucleotide sequence together with the deduced amino acid sequence. The hydropathy profile (18) of the protein sequence (FIG. 2) suggests the presence of seven hydrophobic segments that likely represent the membrane-spanning regions of the receptor which, in conformity with the Genome Database Nomenclature rule, was named CMKRL2.

In particular, the transmembrane regions of the nucleotide sequences depicted in FIG. 1 are indicated by the lines I–VII.

Furthermore, the extracellular domains are believed to be the regions before TMI, between TMII and TMIII, between TMIV and TMV, and between TMVI and TMVII. The extracellular domains are generally believed to be important for ligand and virus binding. The corresponding intracellular domains are the regions between TMI and TMII, between TMIII and TMIV, and between TMV and TMVI, and the tail following TMVII. In general, the intracellular domains are important for coupling of the receptor to the intracellular signaling messengers.

The amino acid sequence shows other features common to the superfamily of G-protein coupled receptors: (i) several consensus sequences for N-linked glycosylation (Asn-X-ser/thr, where X is any amino acid) in the region of the amino terminus (Asn-25, -32, and -44); (ii) a conserved cysteine residue in each of the first two extracellular loops (Cys-130 and Cys-205/207) providing possibilities to form a disulphide bond, which stabilizes the functional protein structure; (iii) proline residues in five of the transmembrane regions (except TMII and TMIII) thought to induce flexibility within the helix formations; and (iv) a carboxyl terminus with several serine and threonine residues (5 and 3, respectively, which could serve as substrate for serine/threonine protein kinases). As indicated by an arrow in the hydropathy profile (FIG. 2), there is a Cys-352 in the last hydrophilic region that may give rise to a palmitoylation, which anchors the carboxyl terminus to the inside of the cell membrane. In embodiments, CyS-352 is deleted.

In one preferred embodiment of the invention, a fragment of the heptahelix receptor comprises a fragment of heptahelix receptor comprising up to about 100 consecutive amino acid residues in FIG. 1 and containing Asn-25, Asn-32, and Asn-44. In another preferred embodiment, a fragment of the heptahelix receptor of the invention comprises a fragment of heptahelix receptor comprising up to about 200 consecutive amino acid residues in FIG. 1 and containing Cys-130 and Cys-205, or Cys-130 and Cys-207, or Cys-205 and Cys-207, or Cys-130 and Cys-205 and Cys-207.

The distribution of the Lymc47-2 message was elucidated in tissues and cell lines by Northern blot hybridization, which detected only one transcript of 2.4 kb size. Under comparable conditions, the strongest signal was found in the Burkitt's lymphoma cell line Raji and in the virus-negative B-cell lymphoma, MC116; a weak signal was also seen in the Burkitt lymphoma cell line Daudi (FIG. 3). No hybridization was found in the other 11 cell lines (partly included in FIG. 3): T-cell lymphoma Jurkat, T-cell leukemias T45 and CCRF, B-cell leukemia 729HF2, promyeloic leukemia HL-60, chronic myelogenous leukemia K-562, lymphoblastic leukemia MOLT-4, HeLa cells S3, colorectal adenocarcinoma SW480, lung carcinoma A549, and melanoma G361.

Besides the high expression in the Burkitt and MC116 lymphoma cells, receptor message of the above size was widespread in peripheral tissues (FIG. 4). Thus, strong hybridization was found in lung, liver (adult and fetal), prostate, and colon; somewhat weaker in heart, pancreas, spleen, ovary, lymph node, and appendix, and a very weak signal was seen in skeletal muscle, kidney, thymus, testicle, and small intestine. Evident also from FIG. 4 is the absence of detectable mRNA in placenta, bone marrow, and in peripheral blood leukocytes. The absent signal in blood was evidenced both from the premade Northern blots and from the blots prepared from peripheral blood mononuclear cells (fractions consisting of lymphocytes without monocytes and B-cells, as well as separate fractions of the two latter cell types).

Since hybridization was seen also in brain (FIG. 4, lane 2), Northern blots from several CNS regions were hybridized with Lymc47-2 cDNA. The 2.4 kb single band appeared with almost identical, moderate signal intensity in all brain regions tested, namely (FIG. 5) cerebellum, cerebral cortex, medulla, spinal cord, occipital lobe, frontal lobe, temporal lobe, putamen, hypothalamus, and (not shown) amygdala, caudate nucleus, corpus callosum, hippocampus, substantia nigra, subthalamic nucleus, and thalamus.

The deduced amino acid sequence was compared (in the GCG/fasta matrix score) with that of the previously cloned Burkitt lymphoma receptors, BLR1 (11) and BLR2 (19), showing 30% overall sequence identity with BLR1 and 25% with BLR2.

Considerable homology to the heptahelix receptor of the invention was also found among known chemoattractant receptors, notably the high-affinity IL8 receptors, which show almost 30% identity. The common motif of the amino acid residues SCLNPLIY (A/S)F (SEQ ID No.5) is seen in the TMVII region of the presently cloned receptor and the IL8 receptors, with a difference in only one amino acid residue between the two isoforms. The novel chemoattractant-like receptor was hence termed CMKRL2.

Homology scores of CMKRL2 compared to the two chemoattractant receptors, which act as coreceptors for HIV-1, showed 27% identity for the LCI1 (19), now termed CXCR4, and 30% for CC CKR5 (20), now termed CCR5. The mutual degree of homology between the two coreceptors turned out to be 30%.

Figure 5:
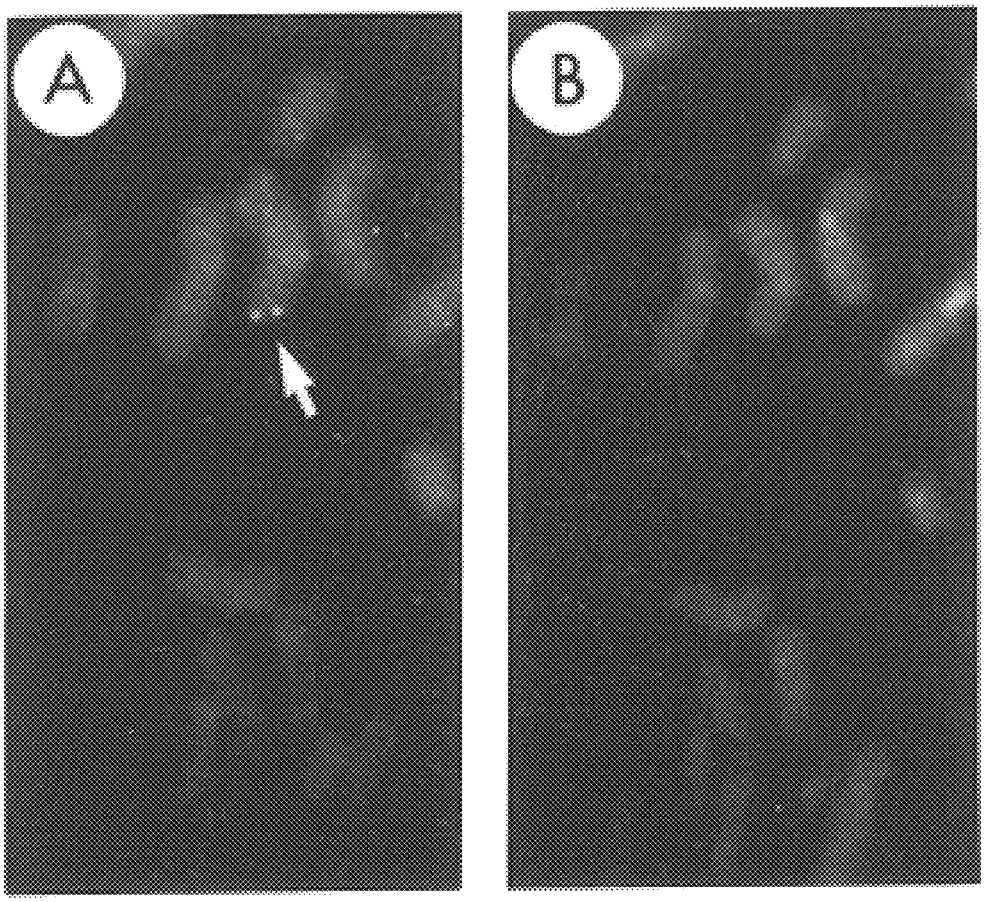

The hybridization efficiency in the chromosome mapping with FISH was 70% (i.e., among 100 checked miotic figures, 70 showed signals on one pair of the chromosome). Based on the DAPI banding, assignment was obtained between the fluorescent signal from the Lymc47-2 cDNA probe and the short arm of chromosome 7 (FIG. 5). The detailed position was further determined as a summation from 10 photographs indicating localization of the corresponding gene to region p22 (FIG. 6).

It will be understood that the heptahelix receptor of the invention and its corresponding DNA template is not limited to the CMKRL2 receptor and Lymc47-2 clones just described. For example, additional cDNA clones can be isolated from cDNA libraries of other mammalian species by cross-species hybridization. Mammalian heptahelix receptor of the present invention includes by way of example, primate, human, murine, canine, feline, bovine, ovine, equine, and porcine heptahelix receptor. Mammalian heptahelix receptors can be obtained by cross-species hybridization using a single-stranded cDNA derived from the human heptahelix receptor DNA sequence as a hybridization probe to isolate heptahelix receptor cDNAs from mammalian cDNA libraries. For use in hybridization, DNA encoding heptahelix receptor can be covalently labeled with a detectable substance, such as a fluorescent group, a radioactive atom, or a chemiluminescent group, by methods well known to those skilled in the art. Such probes can also be used for in vitro diagnosis of particular conditions.

Alternative mRNA constructs, which can be attributed to different mRNA splicing events following transcription and which share large regions of identity or similarity with the heptahelix receptors claimed herein, are considered to be within the scope of the present invention.

Derivatives of heptahelix receptor within the scope of the invention include various structural forms of the primary protein, which retain biological activity. Due to the presence of ionizable amino and carboxyl groups, for example, a heptahelix receptor protein can be in the form of acidic or basic salts, or can be in neutral form. Individual amino acid residues can also be modified by oxidation or reduction.

The primary amino acid structure can be modified by forming covalent or aggregative conjugates with other chemical moieties, such as glycosyl groups, lipids, phosphate, acetyl groups, and the like, or by creating amino acid sequence mutants. Covalent derivatives can be prepared by linking particular functional groups to heptahelix receptor amino acid side chains or at the N- or C-termini. Other derivatives of heptahelix receptor within the scope of this invention include covalent or aggregative conjugates of heptahelix receptor or its fragments with other proteins or polypeptides, such as by synthesis in recombinant culture as N-terminal or C-terminal fusions. For example, the conjugated peptide can be a signal (or leader) polypeptide sequence at the N-terminal region of the protein, which co-translationally or post-translationally directs transfer of the protein from its site of synthesis to its site of function inside or outside of the cell membrane or wall (e.g., the yeast α-factor leader). Heptahelix receptor protein fusions can comprise peptides added to facilitate purification or identification of heptahelix receptor (e.g., poly-His).

Heptahelix receptor derivatives can also be used as immunogens, reagents in receptor-based immunoassays, or as binding agents for affinity purification procedures of chemoattractants or other binding ligands. Heptahelix receptor derivatives can also be obtained by cross-linking agents, such as M-maleimidobenzoyl succinimide ester and N-hydroxysuccinimide, at cysteine and lysine residues. Heptahelix receptor proteins can also be covalently bound through reactive side groups to various insoluble substrates, such as cyanogen bromide-activated, bisoxirane-activated, carbonyldiimidazole-activated, or tosyl-activated agarose structures, or by adsorbing to polyolefin surfaces (with or without glutaraldehyde cross-linking). Once bound to a substrate, heptahelix receptor can be used to selectively bind (for purposes of assay or purification) anti-heptahelix receptor antibodies or chemoattractant.

The present invention also includes heptahelix receptor, with or without associated native-pattern glycosylation. Heptahelix receptor expressed in yeast or mammalian expression systems can be similar or slightly different in molecular weight and glycosylation pattern than the native molecules, depending upon the expression system. Expression of heptahelix receptor DNAs in bacteria, such as $E.\ coli$, provides non-glycosylated molecules. Functional mutant analogs of mammalian heptahelix receptor having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems.

Heptahelix receptor derivatives can also be obtained by mutations of heptahelix receptor or its subunits. A heptahelix receptor mutant, as referred to herein, is a polypeptide homologous to heptahelix receptor, but which has an amino acid sequence different from native heptahelix receptor because of a deletion, insertion, or substitution.

Bioequivalent analogs of heptahelix receptor proteins can be constructed by, for example, making various substitutions of residues or sequences, or deleting terminal or internal residues or sequences, or deleting terminal or internal residues or sequences not needed for biological activity. For example, cysteine residues can be deleted (e.g., $Cys^{178}$) or replaced with other amino acids to prevent formation of unnecessary or incorrect intramolecular disulfide bridges upon renaturation. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Substantially similar polypeptide sequences, as defined above, generally comprise a like number of amino acids.

In order to preserve the biological activity of heptahelix receptors, deletions and substitutions will preferably result in homologously or conservatively substituted sequences, meaning that a given residue is replaced by a biologically similar residue. Examples of conservative substitutions include substitution of one aliphatic residue for another, such as Ile, Val, Leu, or Ala for one another, or substitution of one polar residue for another, such as between Lys and Arg; Glu and Asp; or Gln and Asn. Other such conservative substitutions, for example, substitutions of entire regions having similar hydrophobicity characteristics, are well known.

Mutations in nucleotide sequences constructed for expression of analog heptahelix receptor must, of course, preserve the reading frame phase of the coding sequences and preferably will not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed heptahelix receptor mutants screened for the desired activity.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required.

The present invention provides recombinant expression vectors to amplify or express DNA encoding heptahelix receptor. Recombinant expression vectors are replicable DNA constructs that have synthetic or cDNA-derived DNA fragments encoding mammalian heptahelix receptor or bioequivalent analogs operably linked to suitable transcriptional or translational regulatory elements derived from mammalian, microbial, viral, or insect genes. A transcriptional unit generally comprises an assembly of (1) a genetic element or elements having a regulatory role in gene expression, for example, transcriptional promoters or enhancers; (2) a structural or coding sequence, which is transcribed into mRNA and translated into the heptahelix receptor; and (3) appropriate transcription and translation initiation and termination sequences. Such regulatory elements can include an operator sequence to control transcription and a sequence encoding suitable mRNA ribosomal binding sites. The ability to replicate in a host, usually conferred by an origin of replication, and a selection gene to facilitate recognition of transformants can additionally be incorporated.

DNA regions are operably linked when they are functionally related to each other. For example, DNA for a signal peptide (secretory leader) is operably linked to DNA for a polypeptide if it is expressed as a precursor, which participates in the secretion of the polypeptide. A promoter is operably linked to a coding sequence if it controls the transcription of the sequence. A ribosome binding site is operably linked to a coding sequence if it is positioned so as to permit translation. Generally, operably linked means contiguous and, in the case of secretory leaders, contiguous and in reading frame.

Structural elements intended for use in yeast expression systems preferably include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

DNA sequences encoding mammalian heptahelix receptors, which are to be expressed in a microorganism, preferably contain no introns that could prematurely terminate transcription of DNA into mRNA; however, premature termination of transcription may be desirable, for example, where it would result in mutants having advantageous C-terminal truncations. Due to code degeneracy, there can be considerable variation in nucleotide sequences encoding the same amino acid sequence. Other embodiments include sequences capable of hybridizing to the sequences of the provided cDNA under moderately stringent conditions and other sequences hybridizing or degenerate to those that encode biologically active heptahelix receptor polypeptides.

Recombinant heptahelix receptor DNA can be expressed or amplified in a recombinant expression system comprising a substantially homogenous monoculture of suitable host microorganisms, for example, bacteria such as *E. coli*, or yeast such as *S. cerevisiae*, which have stably integrated (by transduction or transfection) a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells that have been transduced or transfected with heptahelix receptor vectors constructed using recombinant DNA techniques. Transformed host cells ordinarily express heptahelix receptor, but host cells transformed for purposes of cloning or amplifying heptahelix receptor DNA do not need to express heptahelix receptor. Expressed heptahelix receptor will be deposited in the cell membrane or secreted into the culture supernatant, depending on the heptahelix receptor DNA selected. Suitable host cells for expression of heptahelix receptor include prokaryotes, yeast, or higher eukaryotic cells under the control of appropriate promoters. Prokaryotes include gram-negative or gram-positive organisms, such as bacteria, for example *E. coli* or bacilli. Higher eukaryotic cells include established cell lines of mammalian origin. Cell-free translation systems can also be employed to produce heptahelix receptor using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (tp) promoter system (Goeddel et al., *Nucl. Acids Res.* 8:40576, 1980; and EPA 36,776), and tac promoter (Maniatis, *Molecular Cloning: A Laboratory Manual*, Cold Spring Harbor Laboratory, p. 412, 1982).

Recombinant heptahelix receptor proteins can also be expressed in yeast hosts, preferably from the Saccharomyces species, such as *S. cerevisiae*. Yeast of other genera, such as Pichia or Kluyveromyces, can also be employed. Yeast vectors will generally contain an origin of replication from the 2 μ yeast plasmid or an autonomously replicating sequence (ARS), promoter, DNA encoding heptahelix receptor, sequences for polyadenylation, transcription, termination, and a selection gene.

Suitable promoter sequences in yeast vectors include the promoters for metallothionein, 3-phosphoglycerate kinase (Hitzeman et al. *J. Biol. Chem.* 255:2073, 1980), or other glycolytic enzymes (Hess et al. *J. Adv. Enzyme Reg.* 7:149, 1968); and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, phosphoglucose isomerase, and glucokinase.

Various mammalian or insect cell culture systems are also advantageously employed to express recombinant protein. Expression of recombinant proteins in mammalian cells is particularly preferred because such proteins are generally correctly folded, appropriately modified, and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa, and BHK cell lines. Mammalian expression vectors can comprise nontranscribed elements, such as an origin of replication, a suitable promoter, and an enhancer linked to the gene to be expressed, and other 5' or 3' nontranslated sequences, such as ribosome binding sites and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells can be provided by viral sources. For example, commonly used promoters and enhancers are derived from polyoma, adenovirus 2, Simian virus 40 (SV40), and human cytomegalovirus. DNA sequences derived from the SV40 viral genome, for example, SV40 origin, early and late promoter, enhancer, splice, and polyadenylation sites, can be used to provide the other genetic elements required for expression of a heterologous DNA sequence.

Purified mammalian heptahelix receptors or analogs can be prepared by culturing suitable host/vector systems to express the recombinant translation products of the DNAs of the present invention, which are then purified from culture media or cell extracts. For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a heptahelix or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose, or other types commonly employed in protein purification.

Finally, one or more reverse-phase high performance liquid chromatography (RP-HPLC) steps employing hydrophoic RP-HPLC media, e.g., silica gel having pendant methyl or other aliphatic groups, can be employed to further purify a heptahelix receptor-containing composition. Some or all of the foregoing purification steps, in various combinations, can also be employed to provide a homogeneous heptahelix receptor.

Recombinant heptahelix receptor produced in bacterial culture can be isolated by initial extraction from cell pellets, followed by one or more concentration, salting-out, aqueous ion exchange, or size exclusion chromatography steps. Finally, high performance liquid chromatography (HPLC) can be employed for final purification steps. Microbial cells employed in expression of the receptor can be disrupted by any convenient method, including freeze-thaw cycling, sonication, mechanical disruption, or use of cell lysing agents.

Heptahelix receptors synthesized in recombinant culture are characterized by the presence of non-human cell components, including proteins, in amounts and of a character that depend upon the purification steps taken to recover the receptor from the culture. These components ordinarily will be of yeast, prokaryotic, or non-human higher eukaryotic origin and preferably are present in innocuous contaminant quantities, on the order of less than about 1 percent by weight. Further, recombinant cell culture enables the production of heptahelix receptor free of proteins that may be normally associated with receptor as it is found in nature in its species of origin, e.g., in cells, cell exudates, or body fluids.

The present invention provides methods of using therapeutic compositions comprising an effective amount of soluble heptahelix receptor and a suitable diluent or carrier, and methods for modulating heptahelix receptor-dependent responses in humans comprising administering an effective amount of soluble heptahelix receptor to a patient. Appropriate dosages can be determined in trials. The amount and frequency of administration will depend, of course, on such factors as the nature and severity of the indication being treated, the desired response, the condition of the patient, and so forth.

A preferred embodiment of the invention will now be described in still greater detail in the following Examples. These examples are offered by way of illustration, and not by way of limitation.

EXAMPLE 1

Isolation of cDNA Clone

Plasmid preparation was made by cesium chloride-ethidium bromide banding from a CDNA library of human B-cell lymphoblasts (GM 3299; NIGMS Human Genetic Mutant Cell Repository, Camden, N.J.) based on the pCD vector. It was used as template (1 pg) in polymerase chain reactions (PCR) attempting to amplify a DNA segment between the putative TMII and TMVI regions of G-protein coupled receptors as previously described in detail (12). On the basis of sequence stretches in the PCR clone, two 48-base pair oligonucleotides were synthesized, one designated Lym1, 5'-GAAGGTGCACAGGACGGCGATGTCGTAGTACC GCTCGTGCAGGTTGAA-(SEQ ID NO. 3)3'; and the other Lym2, 5'-CCGGGCGTGGTGCTTGGTGCGGAACAGGCTGC AGCGCATCATGGCCCT-(SEQ ID NO. 4)3'. They were labeled with ($\gamma$-$^{32}$p) -ATP and used together as probes to screen pools of recombinants prepared from consecutive dilutions of the cDNA library. Southern blots were hybridized in 3×SSC at 60° C. and the filters were washed in 1×SSC at the same temperature. A positive band of 3.5 kb size was followed until a single clone (designated Lymc47-2) was obtained. Overlapping restriction fragments were subcloned into M13 phage vectors for sequencing of both cDNA strands. Sequence analysis and comparisons were performed with Genetics Computer Group software (University of Wisconsin) and GenBank as well as with the GeneWorks program from IntelliGenetics (Mountain View, Calif.).

EXAMPLE 2

Chromosome Mapping

The procedures followed were those of Heng and Tsui (13,14). Human cord blood lymphocytes were cultured for 68–72 hr, synchronized with BrdU (Sigma), washed with serum-free medium to release the block, and re-cultured with thymidine (2.5 µg/ml, Sigma). Cells were harvested and suspensions dropped on slides using standard procedures, including hypotonic treatment, fixation, and air-drying. The entire plasmid construct (pCD vector with the Lymc47-2 cDNA insert) was used as probe and biotinylated with DATP. For detection with fluorescence in situ hybridization (FISH), the slides were baked at 55° C. for 1 hr, and after RNaseA treatment, they were denatured in 70% formamide in 2×SSC for 1 min at 70° C. and dehydrated with ethanol. The probe was denatured at 75° C. for 5 min in a hybridization mix consisting of 50% formamide, 10% dextran sulphate, and human cot I DNA (BRL). After overnight hybridization, the slides were washed and the hybridization signal recorded in a fluorescence microscope, photographed, and amplified (13). The assignment of FISH mapping data with chromosomal bands was achieved by superimposing FISH signals with chromosomes stained with 4'-6-diamidino-2-phenyl-indole (DAPI). Chromosome mapping results were evaluated in the Genome Data Base (GDB 6.0) and the NCBI database (Online Mendelian Inheritance in Man; OMIM).

EXAMPLE 3

Tissue Distribution of Receptor Message

Total RNA was isolated from human blood cells or tumor cell lines. Peripheral blood mononuclear cells were purified by centrifugation on a Ficoll cushion. Following 1 hr incubation of the cell suspension at 37° C. in plastic bottles, the monocytes became separated by attaching to the bottom. B-cells were then positively selected among cells remaining in suspension using Dynabeads M-450 coated with CD19 mAb, followed by detachment with Detachabead CD19 (both from DYNAL, Oslo). Isolated B-cells, which characteristically remain inactive, showed 97% purity as revealed by flow cytometry. RNA was isolated by acid guanidium thiocyanate-chloroform extraction, denatured, and separated by electrophoresis in a 1% agarose-formaldehyde gel, followed by transfer to Hybond-N (Amersham) nylon membranes and crosslinking by baking at 80° C. For all human tissues and some of the cell lines listed, premade nylon multiple tissue filters from Clontech (Palo Alto) were used (MTN Blot I and II, HBMT I and II, HISM, HCCL). All hybridization was carried out overnight at 42° C. in 5×SSPE, 5×Denardt's solution, 50% formamide, 150 µg/ml denatured salmon sperm, and filters were washed at 60° in finally 0.1×SSC with 0.1% SDS. The hybridization probe consisted of isolated and phenol-purified full-length Lymc47-2 CDNA labeled with ($\alpha$-$^{32}$p)-CTP by random priming (Megaprime, Amersham). Blots were exposed to Kodak XAR film with intensifying screens at −70° C. for 4 days.

In summary, this invention provides a new heptahelix receptor of the chemokine receptor family, which is capable of binding other ligands. The receptor and the polynucleotides encoding the receptor are useful indications of Burkitt's lymphoma because of their expression in such cells.

REFERENCES

The following publications have been cited in the foregoing text and have been identified by a numeral in parentheses, each numeral corresponding to the respective publication in the following list. The entire disclosure of each of the following publications is relied upon and incorporated by reference herein.

1. Watson, S., and Arkinstall, S. (1994) The G-Protein Linked Receptor FactsBook, Academic Press, London.
2. Murphy, P. M. (1994) *Ann. Rev. Immunol.* 12, 593–633.
3. Schall, T. J., and Bacon, K. B. (1994) *Curr. Biol.* 6, 865–873.
4. Slack, J. L., Armitage, R. J., Ziegler, S. F., Dower, S. K., and Gruss, H.-J. (1995) *Int. Immunol.* 7, 1087–1092.
5. Hamann, J., Eichler, W., Hamann, D., Kerstens, H. M. J., Poddighe, P. J., Hoovers, J. M. N., Hartmann, E., Strauss, M., and van Lier, R. A. W. (1995) *J. Immunol.* 155, 1942–1950.
6. Chee, M. S., Satchwell, S. C., Preddie, E., Weston, K. M., and Barrell, B. G. (1990) *Nature* 344, 774–777.
7. Neote, K., DiGregorio, D., Mak, J. Y., Horuk, R., and Shall, T. J. (1993) *Cell* 72, 415–425.
8. Ahuja, S. K., and Murphy, P. M. (1993) *J. Biol. Chem.* 268, 20691–20694.
9. Weiss, R. A. and Clapham, P. R. (1996) *Nature* 381, 647–648.
10. Hill, C. M., and Littman, D. R. (1996) *Nature* 382, 668–669.
11. Dobner, T., Wolf, I., Emrich, T., and Lipp, M. (1992) *Eur. J. Immunol.* 22, 2795–2799.
12. Owman, Ch., Nilsson, Ch., and Lolait, S. J. (1996) *Genomics* 37, 187–194.
13. Heng, H. H. Q., and Tsui, L.-C. (1993) *Chromosoma* 102, 325–332.
14. Heng, H. H. Q., and Tsui, L.-C. (1994) in Methods of Molecular Biology: In Situ Hybridization Protocols (Choo, K. H. A., Ed.), pp. 35–49, Humana Press, Clifton, N.J.
15. König, M., Mahan, L. C., Marsh, J. W., Fink, J. S., and Brownstein, M. J. (1991) *Mol. Cell Neurosci.* 2, 331–337.
16. Brooker, G., Harper, J. F., Teraski, W. L., and Moylan, R. O. (1979) *Adv. Cycl. Nucleotide Res.* 10, 1–33.
17. Kozak, M. (1996) *Cell* 44, 283–292.
18. Kyte, J., and Doolittle, R. F. (1982) *J. Mol. Biol.* 157, 105–132.
19. Burgstahler, R., Kempkes, B., Steube, K., and Lipp, M. (1995) *Biochem. Biopys. Res. Commun.* 215, 737–743.
20. Herzog, H., Hjort, Y. J., Shine, J., and Selbie, L. A. (1993) *DNA and Cell Biol.* 12, 465–471.
21. Samson, M., Labbe, O., Mollereau, C., Vasart, G., and Permentier, M. (1996) *Biochemistry* 35, 3362–3367.
22. Forster, R., Emrich, T., Kremmer, E., and Lipp, M. (1994) *Blood* 84, 830–840.
23. Bowcock, A. M., Kidd, J. R., Lathrop, G. M., Daneshvar, L., May, L. T., Ray, A., Sehgal, P. B., Kidd, K. K., and CavalliSforza, L. L. (1988) *Genomics* 3, 8–16.
24. Taylor, M. W., Long, T., Martinez-Valdez, H., Downing, J., and Zeige, G. (1984) *Proc. Natl. Acad. Sci. USA* 81, 4033–4036.
25. Birkenbach, M., Josefsen, K., Yalamanchili, R., Lenoir, G., and Kieff, E. (1993) *J. Virol.* 67, 2209–2220.
26. Kaiser, E., Forster, R., Wolf, I., Ebensperger, C., Kuehl, W. M., and Lipp, M. (1993) *Eur. J. Immunol.* 23, 2532–2539.

What is claimed is:

1. An isolated or purified heptahelix receptor having a sequence comprising the sequence of SEQ ID NO:2.

2. The heptahelix receptor of claim 1, wherein said receptor is covalently bound to at least one separate and distinct chemical moiety.

3. The heptahelix receptor of claim 2, wherein said chemical moiety is selected from the group consisting of a glycosyl group, a lipid, a phosphate, an acetyl group, a protein, and a polypeptide.

4. The heptahelix receptor of claim 3, wherein said polypeptide is a signal or leader polypeptide.

5. The heptahelix receptor of claim 2, wherein said chemical moiety is covalently bound to the N-terminal or C-terminal residue of said heptahelix receptor.

6. The heptahelix receptor of claim 1, wherein said receptor is derivatized using cross-linking agents.

7. The heptahelix receptor of claim 1, wherein said receptor is covalently bound through reactive side groups to an insoluble substrate.

8. A method of detecting a molecule that binds to a heptahelix cell-surface receptor present on Burkitt's lymphoma cells, said method comprising exposing a cell that displays a cell-surface protein having a sequence comprising SEQ ID NO:2 to a molecule, and determining whether said molecule binds to said cell-surface protein by determining whether there is a change in the signal transduction activity of said cell-surface protein in the presence of said molecule as compared to the absence of said molecule.

9. A method of detecting a molecule that specifically binds to a heptahelix cell-surface receptor present on Burkitt's lymphoma cells, said method comprising isolating or purifying a heptahelix receptor having a sequence comprising SEQ ID NO:2, exposing said receptor to said molecule under conditions wherein said molecule selectively binds to said receptor, and determining whether said molecule is bound to said receptor.

10. An isolated or purified heptahelix receptor comprising all amino acid residues of the sequence of SEQ ID NO:2, wherein residue Cy-352 is deleted or substituted.

* * * * *

SEQUENCE LISTING

<160> NUMBER OF SEQ ID NOS: 5

<210> SEQ ID NO 1
<211> LENGTH: 1128
<212> TYPE: DNA
<213> ORGANISM: Homo sapiens

<400> SEQUENCE: 1

| | | | | | |
|---|---|---|---|---|---|
| atggatgtga | cttcccaagc | ccggggcgtg | ggcctggaga | tgtacccagg | caccgcgcag | 60 |
| cctgcggccc | caacaccac | ctcccccgag | ctcaacctgt | cccacccgct | cctgggcacc | 120 |
| gccctggcca | atgggacagg | tgagctctcg | gagcaccagc | agtacgtgat | cggcctgttc | 180 |
| ctctcgtgcc | tctacaccat | cttcctcttc | cccatcggct | ttgtgggcaa | catcctgatc | 240 |
| ctggtggtga | acatcagctt | ccgcgagaag | atgaccatcc | cgacctgta | cttcatcaac | 300 |
| ctggcggtgg | cggacctcat | cctggtggcc | gactccctca | ttgaggtgtt | caacctgcac | 360 |
| gagcggtact | acgacatcgc | cgtcctgtgc | accttcatgt | cgctcttcct | gcaggtcaac | 420 |
| atgtacagca | gcgtcttctt | cctcacctgg | atgagcttcg | accgctacat | cgccctggcc | 480 |
| agggccatgc | gctgcagcct | gttccgcacc | aagcaccacg | cccggctgag | ctgtggcctc | 540 |
| atctggatgg | catccgtgtc | agccacgctg | gtgcccttca | ccgccgtgca | cctgcagcac | 600 |
| accgacgagg | cctgcttctg | tttcgcggat | gtccgggagg | tgcagtggct | cgaggtcacg | 660 |
| ctgggcttca | tcgtgccctt | cgccatcatc | ggcctgtgct | actccctcat | tgtccgggtg | 720 |
| ctggtcaggg | cgcaccggca | ccgtgggctg | cggccccggc | ggcagaaggc | gctccgcatg | 780 |
| atcctcgcgg | tggtgctggt | cttcttcgtc | tgctggctgc | cggagaacgt | cttcatcagc | 840 |
| gtgcacctcc | tgcagcggac | gcagcctggg | gccgctccct | gcaagcagtc | tttccgccat | 900 |
| gcccaccccc | tcacgggcca | cattgtcaac | ctcgccgcct | ctccaacag | ctgcctaaac | 960 |
| cccctcatct | acagctttct | cggggagacc | ttcagggaca | agctgaggct | gtacattgag | 1020 |
| cagaaaacaa | atttgccggc | cctgaaccgc | ttctgtcacg | ctgccctgaa | ggccgtcatt | 1080 |
| ccagacagca | ccgagcagtc | ggatgtgagg | ttcagcagtg | ccgtgtag | | 1128 |

<210> SEQ ID NO 2
<211> LENGTH: 375
<212> TYPE: PRT
<213> ORGANISM: Homo sapiens

<400> SEQUENCE: 2

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
                20                  25                  30

Leu Ser His Pro Leu Leu Gly Thr Ala Leu Ala Asn Gly Thr Gly Glu
            35                  40                  45

Leu Ser Glu His Gln Gln Tyr Val Ile Gly Leu Phe Leu Ser Cys Leu
        50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375

<210> SEQ ID NO 3
<211> LENGTH: 48
<212> TYPE: DNA
<213> ORGANISM: Homo sapiens

<400> SEQUENCE: 3
gaaggtgcac aggacggcga tgtcgtagta ccgctcgtgc aggttgaa                          48

<210> SEQ ID NO 4
<211> LENGTH: 48
<212> TYPE: DNA
<213> ORGANISM: Homo sapiens

<400> SEQUENCE: 4
ccgggcgtgg tgcttggtgc ggaacaggct gcagcgcatc atggccct                          48

<210> SEQ ID NO 5
<211> LENGTH: 10
<212> TYPE: PRT
<213> ORGANISM: Homo sapiens
<220> FEATURE:
<221> NAME/KEY: UNSURE
<222> LOCATION: (9)

```
<223> OTHER INFORMATION: X AT POSITION 9 IS EITHER S OR A

<400> SEQUENCE: 5

Ser Cys Leu Asn Pro Leu Ile Tyr Xaa Phe
1               5                   10
```